US006626867B1

(12) United States Patent
Christenson et al.

(10) Patent No.: US 6,626,867 B1
(45) Date of Patent: Sep. 30, 2003

(54) IMPLANTABLE DRUG INFUSION DEVICE WITH PERISTALTIC PUMP USING TUBE GUIDES

(75) Inventors: Steven R. Christenson, Coon Rapids, MN (US); Reginald D. Robinson, Plymouth, MN (US); James M. Haase, Blaine, MN (US); Manfred K. Lüedi, Köniz (CH)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,154

(22) Filed: Apr. 28, 2000

(51) Int. Cl.⁷ ................................................ A61M 1/00
(52) U.S. Cl. ..................................... 604/153; 417/477.7
(58) Field of Search ......................... 604/288.04, 93.01, 604/95.01, 131, 132, 134, 151, 153, 890.1, 891.1; 417/477.1, 477.3, 477.5, 477.7, 477.8, 474, 476

(56) References Cited

U.S. PATENT DOCUMENTS

| | | |
|---|---|---|
| 2,804,023 A | 8/1957 | Lee ............................. 103/149 |
| 2,920,578 A | 1/1960 | Schaurte |
| 3,644,068 A | 2/1972 | Lepak ......................... 417/477 |
| 3,822,948 A | 7/1974 | Handl |
| 3,885,894 A | 5/1975 | Sikes .......................... 417/477 |
| 3,918,453 A | 11/1975 | Leonard |
| 3,927,955 A | 12/1975 | Spinosa et al. |
| 3,960,466 A | 6/1976 | Taylor ......................... 417/234 |
| 3,963,023 A | 6/1976 | Hankinson |
| 3,990,444 A | 11/1976 | Vial |
| 4,012,177 A | 3/1977 | Yakich |
| 4,013,074 A | 3/1977 | Siposs ......................... 128/260 |
| 4,256,437 A | 3/1981 | Brown |

(List continued on next page.)

FOREIGN PATENT DOCUMENTS

| | | |
|---|---|---|
| DE | 2452771 A1 | 5/1976 |
| DE | 101 19391 | 4/2001 |
| EP | 0 174 535 A1 | 3/1986 |
| EP | 0 239 255 | 2/1987 |
| EP | 0320441 | 10/1988 |
| EP | 547550 A1 | 12/1989 |
| FR | 2 021 524 | 7/1970 |
| FR | 2 644 853 A1 | 9/1990 |
| FR | 2 719 873 A1 | 5/1994 |
| FR | 2 808 203 | 3/2001 |
| GB | 681 | 1/1902 |

OTHER PUBLICATIONS

U.S. patent application Ser. No. 09/834,874, entitled "Implantable Drug Delivery Device With Peristaltic Pump Having a Retracting Roller", filed Apr. 13, 2001. (P–9175.00) 1173886899.
U.S. patent application Ser. No. 09/835,208, entitled "Implantable Drug Delivery Device With Peristaltic Pump Having a Bobbin Roller Assembly", filed Apr. 13, 2001. (P–9274) 97.
U.S. patent application Ser. No. 09/561,583, entitled "Spring Loaded Implantable Drug Infusion Device", filed Apr. 28, 2000. (P–8901.00) 09561583.
"STA–PURE peristaltic pump tube," Watson–Marlow Bredel product brochure.
"OEM: Peristaltic Pumps for Engineers," Watson–Marlow Limited product brochure.
"OEM: Custom Pump Catalog," Watson–Marlow Bredel product catalog.

*Primary Examiner*—Brian L. Casler
*Assistant Examiner*—Mark K. Han
(74) *Attorney, Agent, or Firm*—Banner & Witcoff, Ltd.

(57) ABSTRACT

An implantable drug infusion device includes a pump tube for holding a liquid to be pumped. A race is configured to support the tube. A roller assembly is configured to compress the tube against the race at one or more points along the path, and the roller assembly includes at least one roller. A tube guide is operably connected to the roller assembly to align the pump tube with respect to a corresponding roller.

18 Claims, 6 Drawing Sheets

U.S. PATENT DOCUMENTS

| | | |
|---|---|---|
| 4,525,164 A | 6/1985 | Loeb et al. |
| 4,545,744 A | 10/1985 | Weber et al. |
| 4,564,342 A | 1/1986 | Weber et al. ............... 417/477 |
| 4,576,556 A | 3/1986 | Thompson |
| 4,650,471 A | 3/1987 | Tamari |
| 4,685,902 A | 8/1987 | Edwards et al. |
| 4,692,147 A | 9/1987 | Duggan |
| 4,950,136 A | 8/1990 | Haas et al. |
| 5,064,358 A | 11/1991 | Calari |
| 5,082,429 A | 1/1992 | Soderquist et al. |
| 5,083,908 A | 1/1992 | Gagnebin et al. |
| 5,096,393 A | 3/1992 | Van Steenderen et al. |
| 5,125,801 A | 6/1992 | Nabity et al. |
| 5,213,483 A | 5/1993 | Flaherty et al. |
| 5,215,450 A | 6/1993 | Tamari ....................... 417/474 |
| 5,266,013 A | 11/1993 | Aubert et al. |
| 5,576,503 A | 11/1996 | Nabity et al. |
| 5,578,001 A | 11/1996 | Shah |
| 5,741,125 A | 4/1998 | Neftel et al. |
| 5,752,930 A * | 5/1998 | Rise et al. ................. 604/508 |
| 5,840,069 A | 11/1998 | Robinson |
| 5,915,932 A | 6/1999 | Nabity et al. |
| 6,036,459 A | 3/2000 | Robinson |
| 6,195,887 B1 * | 3/2001 | Danby et al. ............ 29/888.02 |

* cited by examiner

IMPLANTABLE DRUG INFUSION DEVICE WITH PERISTALTIC PUMP USING TUBE GUIDES

RELATED APPLICATIONS

The following applications are related to the present application: "Implantable Drug Delivery Device with Peristaltic Pump Having a Bobbin Roller Arm", assigned Ser. No. 09/835,208, and "Implantable Drug Delivery Device with Peristaltic Pump Having Retractable Rollers, assigned Ser. No. 09/834,874, both of which are being filed herewith.

BACKGROUND OF THE INVENTION

1. Field of the Invention

The present invention relates to an implantable drug delivery device for infusing a therapeutic agent into an organism, and more particularly, relates to an improved peristaltic implantable pump using tube guides for improved alignment of a fluid tube.

2. Description of the Related Art

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in a body, usually through a catheter. These devices are used to provide patients with a prolonged dosage or infusion of a drug or other therapeutic agent.

Active drug infusion devices feature a pump or a metering system to deliver the drug into the patient's system. An example of such a drug infusion pump currently available is the Medtronic SynchroMed programmable pump. Additionally, U.S. Pat. Nos. 4,692,147 (Duggan), 5,840,069 (Robinson), and 6,036,459 (Robinson), assigned to Medtronic, Inc., Minneapolis, Minn., disclose body-implantable electronic drug administration devices comprising a peristaltic (roller) pump for metering a measured amount of drug in response to an electronic pulse generated by control circuitry associated within the device. Each of these patents is incorporated herein by reference in their entirety for all purposes. Such pumps typically include a drug reservoir, a fill port, a peristaltic pump having a motor and a pumphead to pump out the drug from the reservoir, and a catheter port to transport the drug from the reservoir via the pump to a patient's anatomy. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing. The peristaltic pumps use rollers which move along a pump tube, thereby moving liquid through the tube.

The prior art delivery devices, however, are limiting in that the tube may not be properly aligned with respect to the rollers, leading to inefficient occlusion of the tube. Prior art solutions to the alignment problem include placing wings along the tube, which may lead to an increased height of the device, compromise the tubing geometry, and increase the cost and complexity of manufacture of the tube.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion device which features a peristaltic pump having a new configuration, in which a roller assembly of the peristaltic pump includes a tube guide to properly align a pump tube with respect to rollers of the roller assembly.

In accordance with a first aspect, an implantable drug infusion device includes an implantable drug infusion device including a pump tube for holding a liquid to be pumped. A race is configured to support the tube along a path. A roller assembly is configured to compress the tube against the race at one or more points along the path, and the roller assembly includes at least one roller. At least one tube guide is operably connected to the roller assembly to align the pump tube with respect to a corresponding roller.

In accordance with another aspect, an implantable drug infusion device includes a bulkhead having a race. A pump tube having an inlet and an outlet is positioned within the race. A roller assembly is configured to compress the tube against the race at at least one point along the path, and the roller assembly includes at least one roller. A drive assembly drives the roller assembly relative to the tube along the path so as to move a liquid through the tube. At least one tube guide is operably connected to the roller assembly to align the pump tube with respect to a corresponding roller.

From the foregoing disclosure, it will be readily apparent to those skilled in the art, that is, those who are knowledgeable or experienced in this area of technology, that the present invention provides a significant advance over the prior art. Preferred embodiments of the implantable infusion device of the present invention can significantly improve the alignment of a pump tube with rollers of the device. This will allow for increased manufacturing flexibility, decreased cost of tube manufacture, reduced height of the device, and improved performance. These and additional features and advantages of the invention disclosed here will be further understood from the following detailed disclosure of preferred embodiments.

BRIEF DESCRIPTION OF THE DRAWING

Preferred embodiments are described in detail below with reference to the appended drawings. The accompanying drawings, which are incorporated into and form a part of this specification, together with the description, serve to explain the principles of the invention. The drawings are not drawn necessarily to scale, are only for the purpose of illustrating a preferred embodiment of the invention, and are not to be construed as limiting the invention. Some features of the implantable drug infusion device depicted in the drawings have been enlarged or distorted relative to others to facilitate explanation and understanding. The above mentioned and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
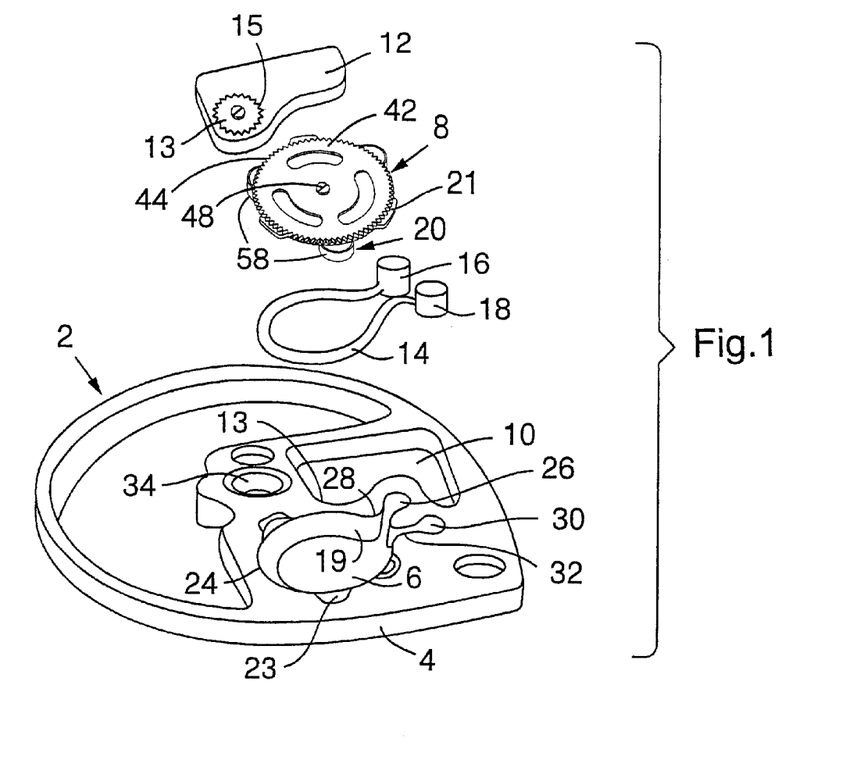
FIG. 1 is an exploded perspective view of an implantable drug infusion device in accordance with the present invention.

As shown in FIG. 1, an implantable drug infusion device 2 in accordance with the invention comprises a bulkhead 4 containing a number of chambers and cavities sized and configured to house various subsystems of the implantable drug infusion device. In particular, bulkhead 4 has a first chamber 6 sized and configured to house a peristaltic pumphead assembly 8. A second chamber 10, sized and configured to house a motor assembly 12 which drives pumphead assembly 8, is positioned adjacent first chamber 6 and separated therefrom by a wall 13. Other chambers of bulkhead 4 house a battery and the electronic circuitry (not shown) used to operate implantable drug infusion device 2 and to control the dosage rate of the medication into the body.

Pumphead assembly 8 includes a compression member, such as roller arm assembly 20, for compressing a pump tube 14 having an inlet 16 and an outlet 18. First chamber 6 has a generally circular wall 24 defining a pump race 19. Pump tube 14 is placed in first chamber 6 in close proximity to wall 24 so that roller arm assembly 20 may force the tube against the wall, thereby forcing medication to move through the tube in a known peristaltic manner. Flanges 21 extending outwardly from pumphead assembly 8 are received in recesses 23 formed in first chamber 6, supporting pumphead assembly 8 in first chamber 6. Inlet 16 is placed in a pump inlet cavity 26 formed in bulkhead 4. Pump inlet cavity 26 is connected to the pump race 19 by a pump inlet race ramp 28. Pump tube outlet 18 is placed in a pump outlet cavity 30 formed in bulkhead 4. Pump tube outlet cavity 30 is connected to the pump race 19 by a pump outlet race ramp 32. In a preferred embodiment, both pump inlet race ramp 28 and pump outlet race ramp 32 have an arcuate geometry. A cover (not shown) is also provided for bulkhead 4 to provide protection for the components of drug infusion device 2. Motor assembly 12 includes a motor (not shown) which drives a four-stage gear assembly 13, only the fourth stage of which is visible. Teeth 15 are formed on the periphery of the fourth stage of gear assembly 13.

Bulkhead 4 has an integral fill port cavity 34, sized and configured to house a septum and components to retain the septum. Drugs are injected through the septum to fill a reservoir (not shown) contained within a lower portion of bulkhead 4. A pathway is formed between the reservoir and pump inlet cavity 28, through which drugs are introduced into pump tube 14. The drugs exit pump outlet cavity 30 and travel through another pathway formed in bulkhead 4 to a catheter port on the periphery of bulkhead 4 from which the drug exits the device 2 and enters the anatomy of the individual. The structure of the septum, retaining components, pathways, and catheter port are known to one of skill in the art and are not shown here.

Figure 2:
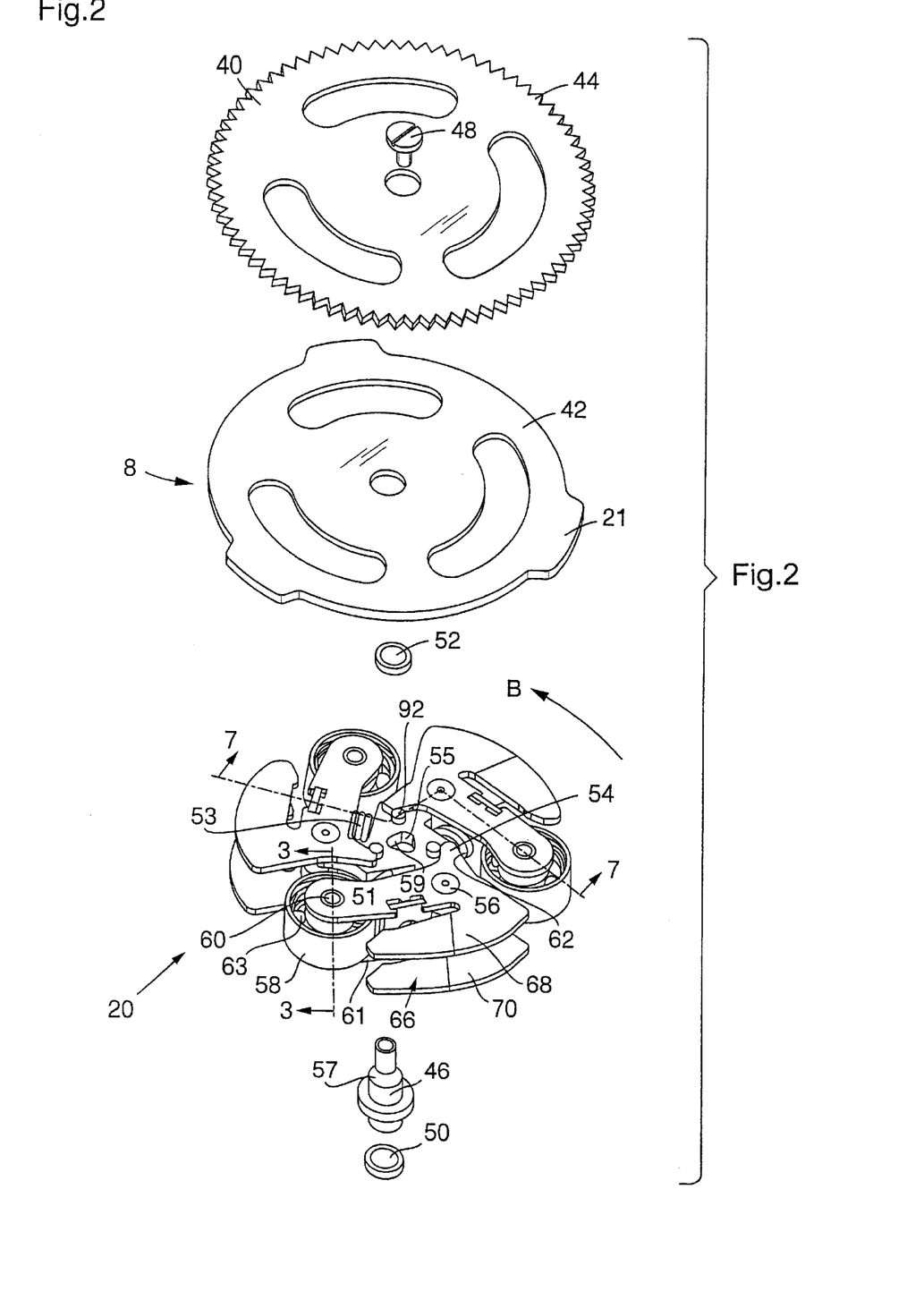
FIG. 2 is an exploded perspective view of a pumphead assembly of the implantable device of FIG. 1.

Referring now to FIG. 2, pumphead assembly 8 is shown in exploded form. Pumphead assembly 8 includes a drive gear 40 with teeth 44 formed about its periphery. A support plate 42 is positioned below drive gear 40. Flanges 21 extend outwardly from support plate 42 and, as described above, are received in recesses 23 of bulkhead 4, and preferably welded thereto. Roller arm assembly 20 is positioned below support plate 42. Drive shaft 46 extends axially through apertures in roller arm assembly 20, support plate 42, and drive gear 40, and is retained by retaining screw 48. Drive shaft 46 is supported for rotation at its lower end by lower bearing 50, and at a central location, between roller arm assembly 20 and support plate 42, by upper bearing 52.

Figure 3:
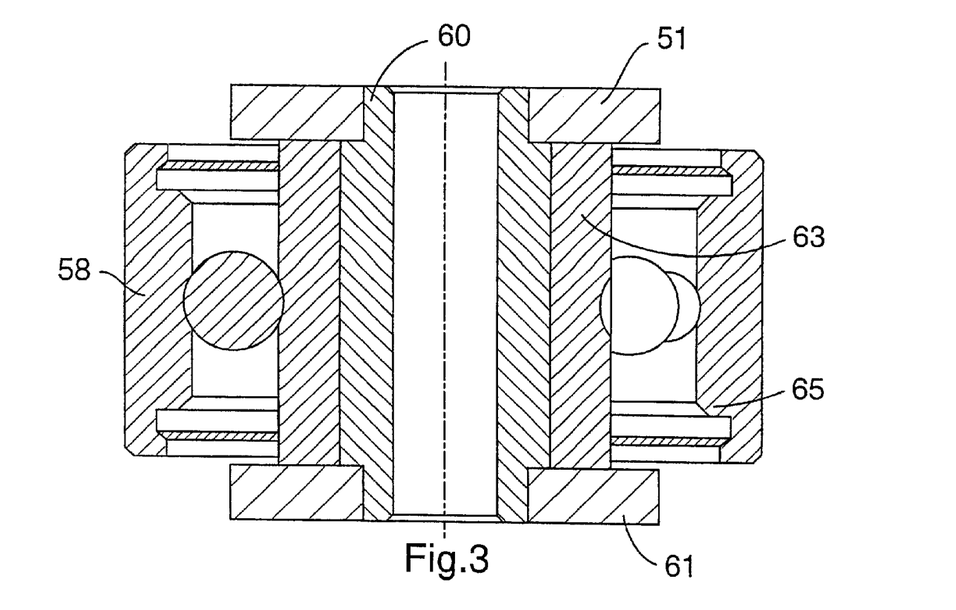
FIG. 3 is a section view, taken along lines 3—3 of FIG. 2, of a trailing arm of the implantable device of FIG. 1.

Roller arm assembly 20 comprises a central hub 53 having an aperture 55 through which drive shaft 46 extends. Flats 57 on drive shaft 46 mate with flats 59 of aperture 55 such that roller arm assembly 20 rotates as drive shaft 46 rotates. A plurality of trailing arms 54 are each pivotally secured by a pin 56 to hub 53. Trailing arm 54 comprises upper plate 51 and lower plate 61. A roller 58 is pivotally secured to each trailing arm 54 by an axle 60. As seen in FIG. 3, axle 60 extends between upper and lower plates 51, 61. Axle 60 passes through an inner race 63 of roller 58. Inner race 63 is extended vertically to provide clearance between an outer race 65 of roller 58 and upper and lower plates 51, 61. In the illustrated embodiment, roller arm assembly 20 is shown with three trailing arms 54 and three corresponding rollers 58, however, the number of trailing arms 54 and rollers 58 may be greater or lesser than three.

Figure 4:
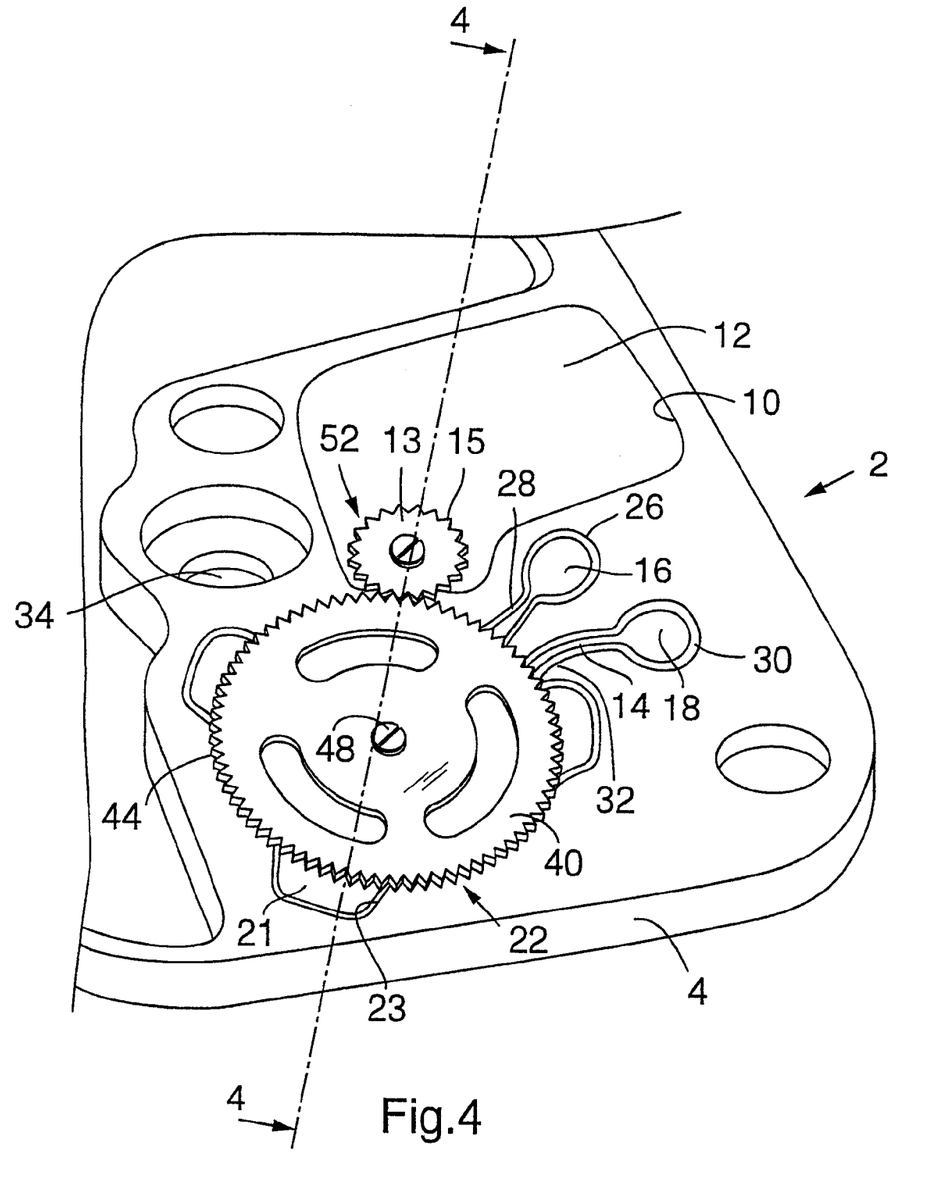
FIG. 4 is perspective view, partially cut away, of the implantable device of FIG. 1, shown in its assembled state.
Figure 5:
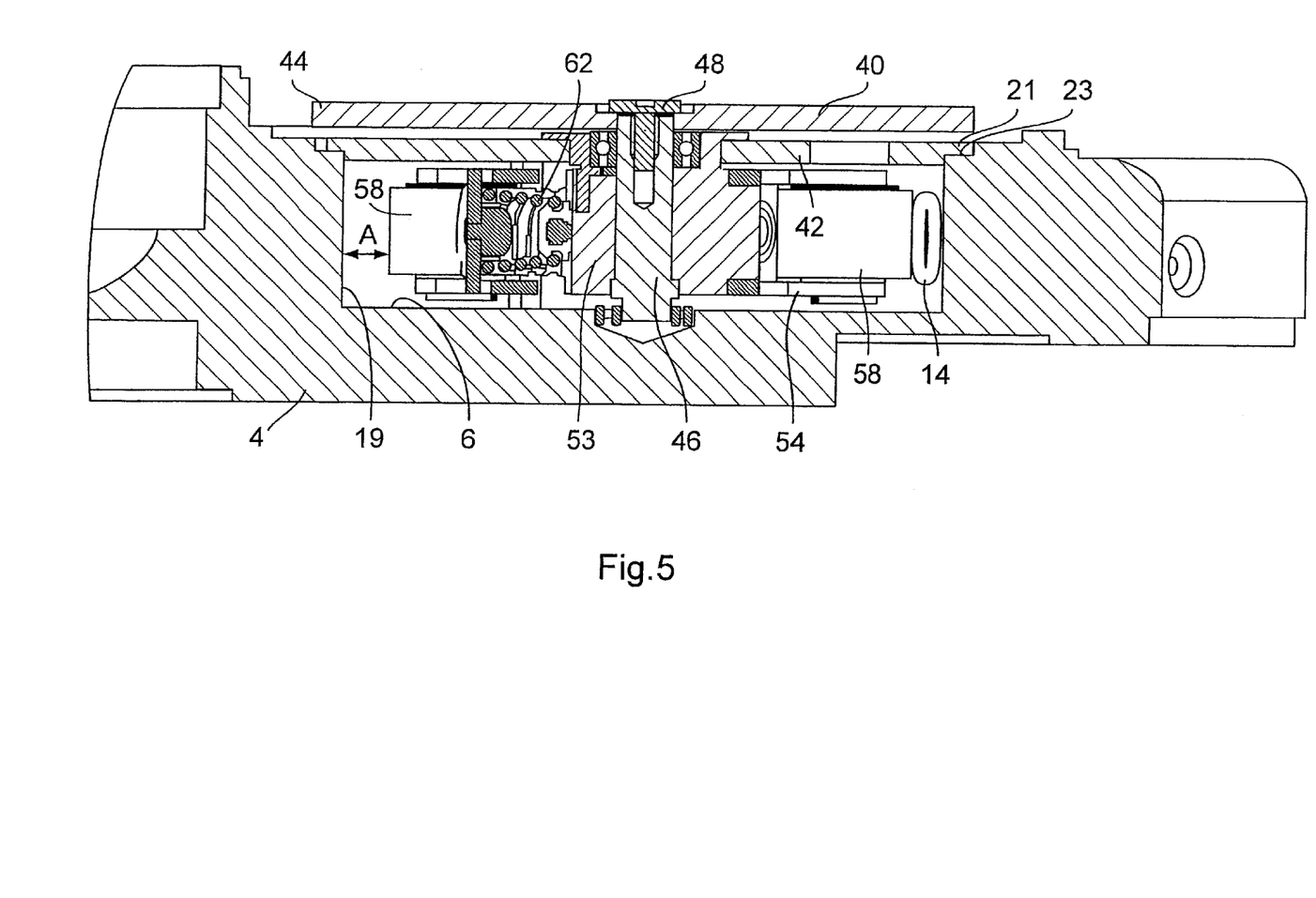
FIG. 5 is a section view, taken along lines 4—4 of FIG. 3, of the implantable device of FIG. 1.

As seen in FIGS. 4 and 5, teeth 15 of gear assembly 13 drivingly engage teeth 44 of drive gear 40, thereby causing rollers 58 to move about race 19, compressing and occluding tube 14 as they move and forcing the drug therethrough in known peristaltic fashion. As noted above, inlet race ramp 28 and outlet race ramp 32 each have an arcuate geometry, which reduces the torque required as each roller 58 engages pump tube 14 during rotation of roller arm assembly 20.

Referring back to FIG. 2, each trailing arm 54 and its corresponding roller 58 is adjustably biased outwardly by a biasing member, such as spring 62. In a preferred embodiment, spring 62 is a coil spring. As seen in FIG. 5, spring 62 is oriented to facilitate the occlusion, or compression, of tube 14 by roller 58. Since manufacturing tolerances on the system components, i.e., roller 58, tube 14 and race 19, can result in variations in the gap A between roller 58 and race 19, the biasing action of spring 62 can advantageously minimize the variation in load placed by roller 58 on tube 14, greatly increasing the compliance of the system. Thus, for an incremental change in the gap between roller 58 and race 19, the incremental load required is reduced. For example, in prior art devices, where the system compliance is accounted for by the tube itself, a 0.001" decrease in a radial direction of the race could incur a 150 g load increase on roller 58. With the present invention, however, spring 62 may be sized with a spring rate such that for a 0.001" decrease in the race, a 1.5 g increase in load is realized. In a preferred embodiment, spring 62 is formed of a highly corrosion resistant and fatigue resistant alloy. Suitable materials include cobalt alloys and stainless steel. In other preferred embodiments, a nitinol shape memory alloy may be used for spring 62.

Figure 6:
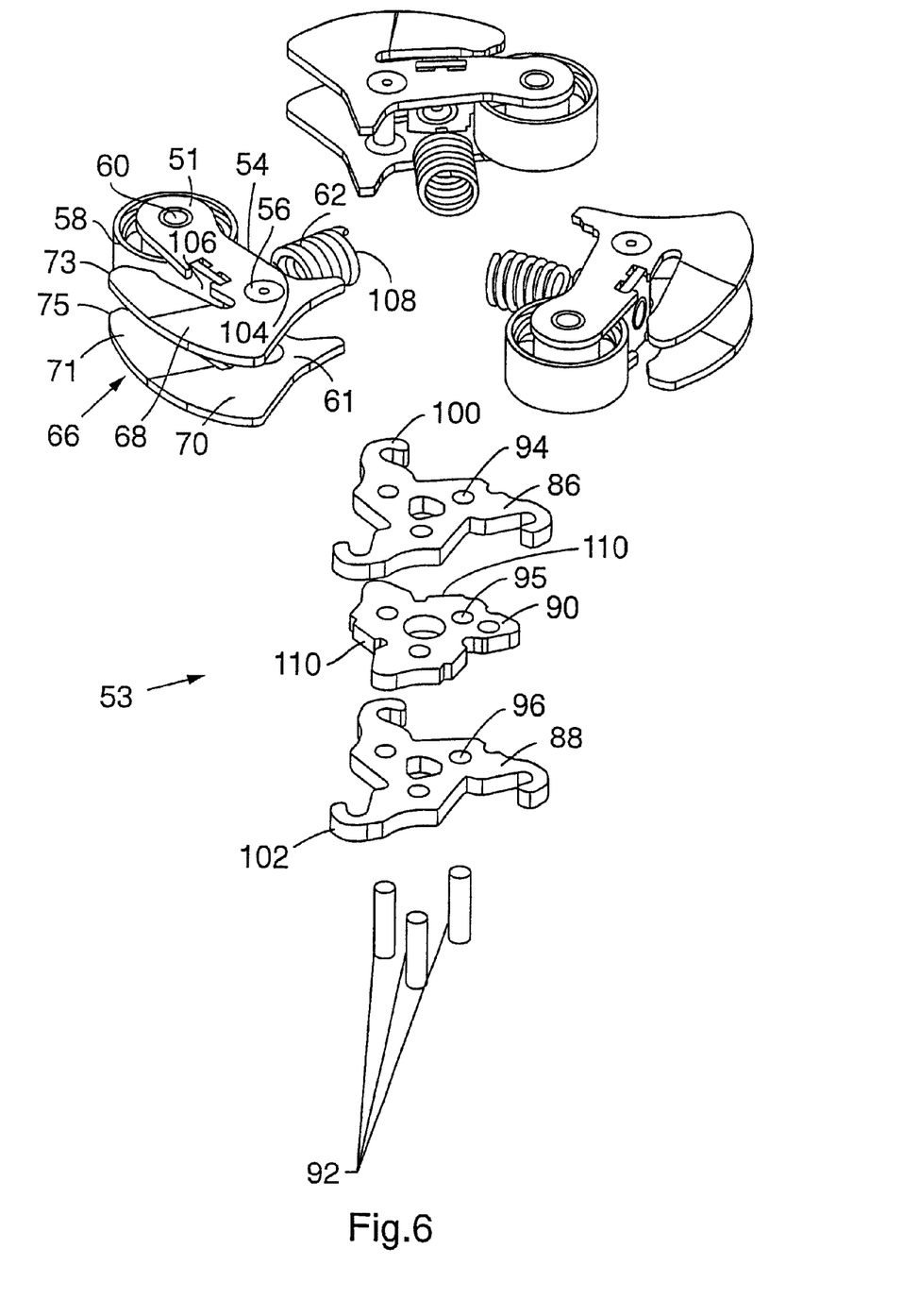
FIG. 6 is an exploded perspective view of the roller assembly of FIG. 1.
Figure 7:
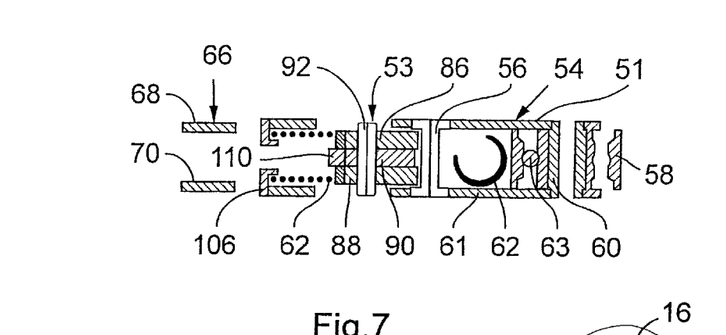
FIG. 7 is a section view, taken along lines 7—7 of FIG. 2, of a trailing arm of the implantable device of FIG. 1.

Roller arm assembly is shown in exploded form in FIG. 6. As noted above, roller arm assembly 20 comprises three trailing arms 54 pivotally secured by a pin 56 to hub 53. Hub 53 comprises upper plate 86, lower plate 88, and center plate 90. Rods or rivets 92 extend through apertures 94, 95, and 96 formed in upper plate 86, center plate 90, and lower plate 88, respectively. Pivot pins 56 extend between upper plate 51 and lower plate 61 of each trailing arm 54. Hooks 100, 102 formed on upper plate 86 and lower plate 88, respectively, of hub 53, capture pivot pins 56 of trailing arms 54. A first end 104 of each spring 62 seats on mounting plate 106 of trailing arm 54. A second end 108 of each spring 62 seats about a rib 110 formed on center plate 90 of hub 53, as can be seen more clearly in FIG. 7. The force of spring 62 exerted outwardly from hub 53 keeps pin 56 seated within hooks 100 and 102, thereby maintaining trailing arms 54 in position on hub 53. By using hooks 100 and 102 to capture pins 56 of trailing arms 54 rather than apertures, the manufacturing costs of hub 53 can be reduced, and very close tolerances can be achieved, improving manufacturing flexibility.

Figure 8:
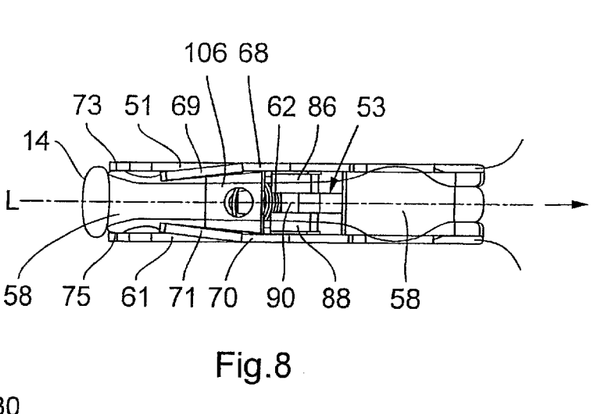
FIG. 8 is an elevation view of a trailing arm of the implantable device of FIG. 1.

As seen in FIGS. 6 and 8, a tube guide 66 is connected to trailing arm 54 and is formed of an upper blade 68 and a lower blade 70. In another preferred embodiment, tube guide 66 may be connected directly to hub 53. A rear portion 69 of upper blade 68 is inclined downwardly, with respect to a longitudinal axis L of pump tube 14 (shown here in dashed lines), toward a trailing edge 73 of upper blade 68. A rear portion 71 of lower blade 70 is inclined upwardly, with respect to a longitudinal axis L of pump tube 14, toward a trailing edge 75 of upper blade 68. Tube guide 66 serves to help keep pump tube 14 properly aligned and centered vertically with respect to rollers 58. By using tube guide 66 to align the pump tube any tendency for the pump tube to migrate up or down with respect to the rollers is minimized.

Figure 9:
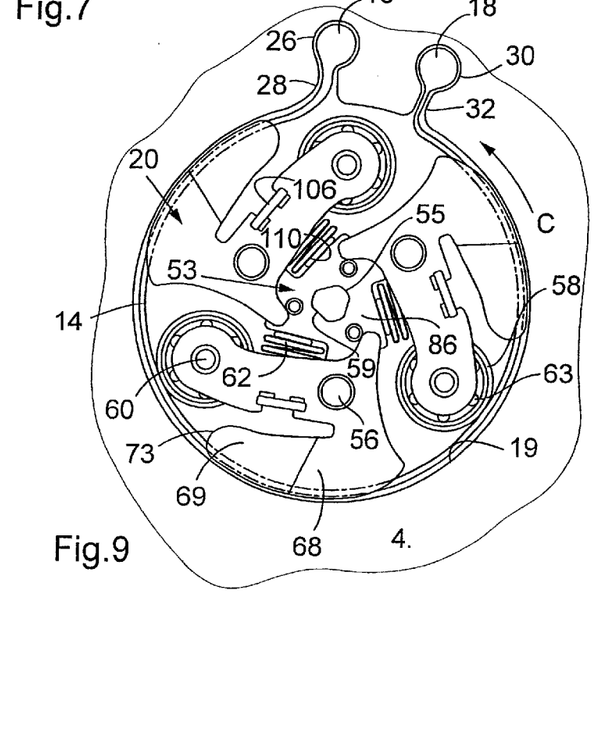
FIG. 9 is a plan view of the roller assembly and pump tube shown in place within the race of the implantable device of FIG. 1.

As seen in FIG. 9, pump tube 14 is positioned between roller assembly 20 and race 19. As roller assembly 20 rotates in the direction of arrow C, rollers 58 compress pump tube 14 against race 19, forcing drug through the pump tube 14. Pump tube 14 is aligned with respect to each roller 58 by a tube guide 66 which is immediately in front of the roller 58 and a tube guide 66 which immediately follows the roller 58. Thus, pump tube 14 is aligned both prior to and after encountering each roller 58, ensuring proper alignment of the pump tube. As each roller 58 passes a section of pump tube 14, the pump tube is occluded by being squeezed by roller 58 against race 19, thereby increasing the vertical height of the pump tube at this point, seen in FIG. 8. Pump tube 14 springs back to its normal cross-section after roller 58 passes, allowing the more closely spaced portions 69, 71 of upper and lower blades 68, 70 to guide pump tube 14. This alignment of pump tube 14 with respect to rollers 58 is advantageously accomplished without the need to modify the geometry of the pump tube, providing for reduced manufacturing costs for the pump tube.

In light of the foregoing disclosure of the invention and description of the preferred embodiments, those skilled in this area of technology will readily understand that various modifications and adaptations can be made without departing from the scope and spirit, of the invention. All such modifications and adaptations are intended to be covered by the following claims.

What is claimed is:

1. an implantable drug infusion device comprising, in combination:
   a pump tube for holding a liquid to be pumped;
   a race configured to support the tube along a path;
   a roller assembly configured to compress the tube against the race at one or more points along the path, the roller assembly including at least two rollers;
   at least one tube guide extending from the roller assembly and from a position immediately adjacent one of the rollers to a position immediately adjacent another of the rollers to align the pump tube with respect to the corresponding rollers.

2. The implantable drug infusion device of claim 1, wherein each tube guide comprises an upper blade and a lower blade.

3. The implantable drug infusion device of claim 2, wherein a portion of the upper blade is inclined downwardly, with respect to a longitudinal axis of the pump tube, toward a trailing edge of the upper blade.

4. The implantable drug infusion device of claim 2, wherein a portion of the lower blade is inclined upwardly, with respect to a longitudinal axis of the pump tube, toward a trailing edge of the lower blade.

5. The implantable drug infusion device of claim 1, wherein the roller assembly comprises at least one trailing arm pivotally connected to the roller assembly, each trailing arm having a roller pivotally secured thereto and a tube guide to align the pump tube with respect to the roller.

6. The implantable drug infusion device of claim 5, wherein the roller assembly comprises three trailing arms.

7. The implantable drug infusion device of claim 5, wherein the roller assembly includes a hub comprising an upper plate, a center plate, and a lower plate, the upper and lower plates each including at least one hooked member, and each trailing arm includes a pivot pin, wherein each hooked member captures a pivot pin of a corresponding trailing arm.

8. The implantable drug infusion device of claim 5, wherein each tube guide comprises an upper blade and a lower blade.

9. An implantable drug infusion device comprising, in combination:
   a bulkhead having a race;
   a pump tube having an inlet and an outlet and being positioned within the race;
   a roller assembly configured to compress the tube against the race at at least one point along the path, the roller assembly including at least two rollers;
   a drive assembly to drive the roller assembly relative to the tube along the path so as to move a liquid through the tube; and
   at least one tube guide extending from the roller assembly and from a position immediately adjacent one of the rollers to a position immediately adjacent another of the rollers to align the pump tube with respect to the corresponding rollers.

10. The implantable drug infusion device of claim 9, wherein each tube guide comprises an upper blade and a lower blade.

11. The implantable drug infusion device of claim 10, wherein a portion of the upper blade is inclined downwardly, with respect to a longitudinal axis of the pump tube, toward a trailing edge of the upper blade.

12. The implantable drug infusion device of claim 10, wherein a portion of the lower blade is inclined upwardly, with respect to a longitudinal axis of the pump tube, toward a trailing edge of the lower blade.

13. The implantable drug infusion device of claim 9, wherein the roller assembly comprises at least one trailing arm pivotally connected to the roller assembly, each trailing arm having a roller pivotally secured thereto and a tube guide to align the pump tube with respect to the roller.

14. The implantable drug infusion device of claim 13, wherein each tube guide comprises an upper blade and a lower blade.

15. An implantable drug infusion device comprising, in combination:
- a bulkhead having a race, a first chamber, and a second chamber;
- a pump tube having an inlet and an outlet and being positioned within the race;
- a motor assembly positioned within the first chamber; and
- a pumphead assembly positioned within the second chamber, the motor assembly driving the pumphead assembly, the pumphead assembly comprising
  - a roller assembly having a hub, three trailing arms, each trailing arm having a roller and being pivotally connected to the hub;
  - a drive assembly to drive the roller assembly relative to the tube along the path so the rollers compress the tube to move a liquid through the tube; and
  - a tube guide extending from each trailing arm and from a position immediately adjacent one of the rollers to a position immediately adjacent another of the rollers to align the pump tube with respect to the corresponding rollers.

16. The implantable drug infusion device of claim 15, wherein each tube guide comprises an upper blade and a lower blade.

17. The implantable drug infusion device of claim 16, wherein a portion of the upper blade is inclined downwardly, with respect to a longitudinal axis of the pump tube, toward a trailing edge of the upper blade.

18. The implantable drug infusion device of claim 16, wherein a portion of the lower blade is inclined upwardly, with respect to a longitudinal axis of the pump tube, toward a trailing edge of the lower blade.

* * * * *